United States Patent [19]

Milstein et al.

[11] Patent Number: 5,540,939
[45] Date of Patent: Jul. 30, 1996

[54] MODIFIED HYDROLYZED VEGETABLE PROTEIN MICROSPHERES AND METHODS FOR PREPARATION AND USE THEREOF

[75] Inventors: Sam J. Milstein, Larchmont; Evgueni Barantsevitch, New Rochelle, both of N.Y.

[73] Assignee: Emisphere Technologies, Inc., Hawthorne, N.Y.

[21] Appl. No.: 233,281

[22] Filed: Apr. 25, 1994

Related U.S. Application Data

[63] Continuation-in-part of PCT/US94/04561, Apr. 22, 1994, which is a continuation-in-part of Ser. No. 51,739, Apr. 22, 1993, Pat. No. 5,401,516, which is a continuation-in-part of Ser. No. 995,508, Dec. 21, 1992, abandoned.

[51] Int. Cl.[6] ............................. A61K 9/16; A61K 9/50
[52] U.S. Cl. ..................... 424/491; 424/489; 424/490
[58] Field of Search ............................... 424/491, 489, 424/488, 490

[56] References Cited

U.S. PATENT DOCUMENTS

| | | |
|---|---|---|
| Re. 24,899 | 11/1960 | Green. |
| 2,671,451 | 3/1954 | Bolger ............................ 128/260 |
| 2,862,918 | 12/1956 | Meyer et al. .................. 260/123.5 |
| 2,868,740 | 1/1959 | Luce ................................... 260/8 |
| 2,971,916 | 2/1961 | Schleicher et al. ............. 252/62.5 |
| 3,016,308 | 1/1962 | Macaulay ........................ 177/37.7 |
| 3,052,655 | 9/1962 | Fox et al. .......................... 260/78 |
| 3,057,344 | 10/1962 | Abella et al. ....................... 128/2 |
| 3,076,790 | 2/1963 | Fox et al. .......................... 260/78 |
| 3,170,802 | 2/1965 | Fukushima ........................ 99/145 |
| 3,190,837 | 6/1965 | Brynko et al. ................... 252/316 |
| 3,474,777 | 10/1969 | Figge et al. ........................ 128/2 |
| 3,491,093 | 1/1970 | Pachter et al. ................ 260/247.5 |
| 3,565,559 | 2/1971 | Sato ................................. 424/37 |
| 3,567,650 | 3/1971 | Bakan .............................. 252/316 |

(List continued on next page.)

FOREIGN PATENT DOCUMENTS

| | | |
|---|---|---|
| 1077842 | 8/1976 | Canada. |
| 0000667A1 | 2/1979 | European Pat. Off. ......... A61K 9/50 |
| 0105804 | 4/1984 | European Pat. Off. ........ C12N 15/00 |
| 0130162A2 | 1/1985 | European Pat. Off. ......... B01J 13/02 |
| 0170540A1 | 2/1986 | European Pat. Off. ......... A61K 9/52 |
| 0342054A2 | 11/1989 | European Pat. Off. ......... A61K 7/06 |
| 0342056A2 | 11/1989 | European Pat. Off. ......... A61K 7/06 |
| 0366277 | 5/1990 | European Pat. Off. ....... A61K 9/107 |
| 0448057 | 9/1991 | European Pat. Off. ........ C12P 21/08 |
| 0452161 | 10/1991 | European Pat. Off. ......... A61K 7/48 |
| 0459795 | 12/1991 | European Pat. Off. ....... A61K 37/02 |
| 0467389 | 1/1992 | European Pat. Off. ......... A61K 9/52 |
| 1351358 | 3/1964 | France. |

(List continued on next page.)

OTHER PUBLICATIONS

Airaudo, C. B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S. W. et al. (1976) *BioSystems*, vol. 8, pp. 40–44.
Fox, S. W. et al., *Molecular Evolution and the Origin of Life*, Maxel Decker, New York (1977).
Fox, S. W. et al. (1968) *Biochim. Biophys. Acta*, vol. 160, pp. 246–249.

(List continued on next page.)

Primary Examiner—Thurman K. Page
Assistant Examiner—William E. Benston, Jr.
Attorney, Agent, or Firm—Darby & Darby, P.C.

[57] ABSTRACT

Modified hydrolyzed vegetable protein microspheres and methods for their preparation and use as oral delivery systems for pharmaceutical agents are described.

13 Claims, 5 Drawing Sheets

5,540,939
Page 2

U.S. PATENT DOCUMENTS

| | | | |
|---|---|---|---|
| 3,574,832 | 4/1971 | Engel et al. | 424/183 |
| 3,576,758 | 4/1971 | Emrick | 252/316 |
| 3,725,113 | 4/1973 | Chang | 117/82 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,895,725 | 1/1990 | Kantor et al. | 424/455 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,055,300 | 10/1991 | Gupta | 424/409 |
| 5,069,936 | 12/1991 | Yen | 427/213.33 |
| 5,100,669 | 3/1992 | Hyon et al. | 424/426 |
| 5,100,918 | 3/1992 | Sunshine et al. | 514/557 |
| 5,126,147 | 6/1992 | Silvestri et al. | 424/497 |
| 5,137,892 | 8/1992 | Chu et al. | 514/278 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,250,236 | 10/1993 | Gasco | 264/4.4 |
| 5,271,961 | 12/1993 | Mathiowitz et al. | 427/213.13 |
| 5,328,992 | 7/1994 | Peter et al. | 534/116 |
| 5,384,133 | 1/1995 | Boyes et al. | 424/491 |
| 5,418,010 | 5/1995 | Janda et al. | 424/491 |

FOREIGN PATENT DOCUMENTS

| | | | |
|---|---|---|---|
| 1468601 | 2/1967 | France . | |
| 2133926 | 12/1972 | France | A61K 27/00 |
| 2326934 | 5/1977 | France | A61K 47/00 |
| 2565102 | 12/1985 | France | A61K 9/52 |
| 2424169 | 12/1974 | Germany | A61K 9/00 |
| 3202255 | 10/1982 | Germany | C08L 89/00 |
| 3612102 | 10/1986 | Germany | C07K 15/00 |
| 71258/2 | 12/1987 | Israel . | |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1075952 | 7/1967 | United Kingdom | A61J 5/02 |
| 1567763 | 5/1980 | United Kingdom | A61K 9/22 |
| WO85/00110 | 1/1985 | WIPO . | |
| WO85/00105 | 1/1985 | WIPO | A61K 9/52 |
| WO87/04076 | 7/1987 | WIPO | A61K 45/02 |
| WO88/01213 | 2/1988 | WIPO | B23B 5/16 |
| 93/18754 | 9/1993 | WIPO | A61K 9/16 |

OTHER PUBLICATIONS

Fox, S. W. (1976) *Origins of Life*, vol. 7, pp. 49–68.

Fox, S. W. (1980) *Naturwissenschaften*, vol. 67, pp. 378–383.

Fox, S. W. et al. (1960) *Archives of Biochemistry and Biophysics*, vol. 86, pp. 281–285.

Fox, S. W. et al. (1974) *Origins of Life*, vol. 5, pp. 227–237.

Fox, S. W. (1984) *Origins of Life*, vol. 14, pp. 485–488.

Gol'dovskii, A. M. (1978) *Zhurnal Evolyutsionnoi Biokhimii i Fiziologii*, vol. 14(6), pp. 517–519.

Gurrieri, S. et al. (1973) *Thermochimica Acta*, vol. 7, pp. 231–239.

Harada, K. et al. (1979) *BioSystems*, vol. 11, pp. 47–53.

Harada et al., (1960) *Archives of Biochemistry and Biophysics*, vol. 86, pp. 274–280.

Hare (1970) *Etude Cenetique De La Polycondensation Thermique D'$_\chi$–Amino Acides*, vol. 45, pp. 330–339.

Heinrich, M. R. et al. (1969) *Archives of Biochemistry and Biophysics*, vol. 130, pp. 441–448.

Heinz, B. et al. (1981) *BioSystems*, vol. 14, pp. 33–40.

Hennon, G. et al. (1975) *Biochimie*, vol. 57, pp. 1395–1396.

Hsu, L. L. et al. (1976) *BioSystems*, vol. 8, pp. 89–101.

Hsu, L. L. et al. (1971) *Currents in Modern Biology*, vol. 4, pp. 12–25.

Ishima, Y. et al. (1981), *BioSystems*, vol. 14, pp. 243–251.

Jackson et al. (1991) "Pharmacological . . . ", *J. Pharm. & Exp. Thera.*, vol. 261, No. 1, pp. 546–552.

Jungck, J. R. et al. (1973) *Naturwissenschaften*, vol. 60, pp. 425–427.

Kokufuta, E. et al. (1984) *BioSystems*, vol. 16, pp. 175–181.

Krampitz, G. et al. (1967) *Naturwissenschaften*, pp. 516–517.

Krampitz, G. et al. (1968) *Naturwissenschaften*, pp. 345 and 346.

Krampitz, G. et al. (1966) *Naturwissenschaften*, pp. 7 and 8.

Lacey, Jr., J. C. et al. (1979) *BioSystems*, vol. 11, pp. 9–17.

Lacey, Jr., J. C. et al. (1979) *BioSystems*, vol. 11, pp. 1–7.

Martinez Luque-Romero, M. et al. (1986) *BioSystems*, vol. 19, pp. 267–272.

Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W. W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V. J. A. (1984) *Origins of Life*, vol. 14, pp. 513–522.
Olafsson, P. G. et al. (1971) *Polymer Letters*, vol. 9, pp. 521–528.
Phillips, R. D. et al. (1974) *Int. J. Peptide Protein Res.*, vol. 6, pp. 309–319.
Przybylski, A. T. et al. (1982) *Die Naturwissenschaften*, vol. 69, pp. 561–563.
Przybylski, A. T. et al. (1984) *Applied Biochemistry and Biotechnology*, vol. 10, pp. 301–307.
Przybylski, A. T. (1985) *BioSystems*, vol. 17, pp. 281–288.
Rohlfing, D. L. (1975) *Origins of Life*, vol. 6, pp. 203–209.
Rohlfing, D. L. (1970) *Science*, vol. 169, pp. 998–1000.
Rohlfing, D. L. (1967) *Archives of Biochemistry and Biophysics*, vol. 118, pp. 468–474.
Rohlfing, D. L. et al. *Catalytic Activities of Thermal Polyanhydro-α-Amino Acids*, pp. 373–418.
Rohlfing, D. L. et al. (1976) *BioSystems*, vol. 8, pp. 139–145.
Ryan, J. W. et al. (1973) *BioSystems*, vol. 5, pp. 115–118.
Saunders, M. A. et al. (1974) *BioSystems*, vol. 6, pp. 81–92.
Snyder, W. D. et al. (1975) *BioSystems*, vol. 7, pp. 222–229.
Sokol, P. E. (1974) *Journal of the American Oil Chemists' Society*, vol. 52, pp. 101–102.
Tschager et al. (1989) *Milchwirtschaftliche Berichte*, vol. 95, pp. 79–83.
Vaughan, G. et al. (1987) *BioSystems*, vol. 20, pp. 219–223.
Vol'kenshtein, M. V. (1989) *Molekulyarnaya Biologiya*, vol. 23(1), pp. 23–37.
Waehneldt, T. V. et al. (1968) *Biochim. Biophys. Acta.*, vol. 160, pp. 239–245. Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
Chemical Abstract, vol. 80(5) Abst. No. 52392a.
Bergeron, Raymond J., et al. (1994) "Macromolecular Self-Assembly of Diketopiperazine Tetrapeptides", *Journal of the American Chemical Society*, vol. 116, pp. 8479–8484.
Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.
Bergeron, Raymond et al., "A Comparative Evaluation of Iron Clearance Models", *Annals New York Academy of Sciences*, pp. 378–393.
Andriuoli, G., et al. (1990), *Haemostasis* 20 (suppl. 1):154–158.
Caramazza, I., et al. (1991), *Thrombosis Research* 62:785–789.
Guarini, S. et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Waldmann [Science 252:1657–1662 (1991)].
Harris et al. [TIBTECH 11:42–44 (1993)].
Osband et al. [Immunotherapy 11(6):193–195 (1990)].
Dillman [Ann. Internal Med. 111:592–600 (1989)].
Hird et al. [Genes and Cancer (1990) chapter 17].
Curti [Critical Reviews in Oncology/Hematology 14:29–39 (1993)].

MODIFIED HYDROLYZED VEGETABLE PROTEIN MICROSPHERES AND METHODS FOR PREPARATION AND USE THEREOF

This is a continuation-in-part of PCT application No. PCT/US94/04/04561, filed Apr. 22, 1994, which is a continuation-in-part of U.S. patent application Ser. No. 08/051,739, filed Apr. 22, 1993, now U.S. Pat. No. 5,401,516 which is a continuation-in-part of U.S. patent application Ser. No. 07/995,508, filed Dec. 21, 1992, abandoned. This invention relates to modified hydrolyzed vegetable proteins and microspheres made from them. The microspheres releasably encapsulate active agents and are suitable for oral administration to mammals. Methods for the preparation of such microspheres are also disclosed.

BACKGROUND OF THE INVENTION

The available means for delivering pharmaceutical and therapeutic agents to mammals often are severely limited by chemical or physical barriers or both, which are imposed by the body. For example, oral delivery of many biologically-active agents would be the route of choice if not for the presence of chemical and physicochemical barriers such as extreme pH in the gut, exposure to powerful digestive enzymes, and impermeability of gastrointestinal membranes to the active ingredient. Among the numerous pharmacological agents which are known to be unsuitable for oral administration are biologically active peptides and proteins, such as insulin. These agents are rapidly destroyed in the gut by acid hydrolysis and/or by proteolytic enzymes.

Much research has been devoted to developing effective oral drug delivery methods and systems for these vulnerable pharmacological agents. The proposed solutions have included:

(a) co-administration of adjuvants (such as resorcinols and non-ionic surfactants polyoxyethylene oleyl ether and n-hexadecyl polyethylene ether to increase the permeability of the intestinal walls; and (b) co-administration of enzymatic inhibitors, such as pancreatic trypsin inhibitor, diisopropylfluorophosphate (DFF) and trasylol to avoid enzymatic degradation.

The use of such substances, in drug delivery systems, is limited however either because of their:

(a) inherent toxicity when employed in effective amounts; or (b) failure to protect the active ingredient or promote its absorption; or (c) adverse interaction with the drug.

Liposomes as drug delivery systems have also been described. They provide a layer of lipid around the encapsulated pharmacological agent. The use of liposomes containing heparin is disclosed in U.S. Pat. No. 4,239,754 and several studies have been directed to the use of liposomes containing insulin; e.g., Patel et al. (1976) *FEBS Letters* Vol. 62, page 60 and Hashimoto et al. (1979) *Endocrinol. Japan,* Vol. 26, page 337. The use of liposomes, however, is still in the development stage and there are continuing problems, including:

(a) poor stability;
(b) inadequate shelf life;
(c) limited to low MW (<30,000) cargoes;
(d) difficulty in manufacturing;
(e) adverse interactions with cargoes.

More recently, artificial amino acid polymers or proteinoids, forming microspheres, have been described for encapsulating pharmaceuticals. For example, U.S. Pat. No. 4,925,673 (the '673 patent), the disclosure of which is hereby incorporated by reference in its entirety, describes such microsphere constructs as well as methods for their preparation and use. The microspheres of the '673 patent are useful for encapsulating a number of active agents, however there is a need in the art for microsphere carriers that can encapsulate a broader range of active agents such as lipophilic drugs.

Additionally, the method employed in the '673 patent for preparing proteinoids results in a complex mixture of high molecular weight (MW) (>1000 daltons) and low MW ($\leq$1000 daltons) peptide-like polymers which are difficult to separate. Moreover, small amounts of the low MW microsphere-forming proteinoids are obtained. Thus, an improved method of preparing low molecular weight sphere-forming proteinoids is also desired.

SUMMARY OF THE INVENTION

The present invention relates to a modified hydrolyzed vegetable protein microsphere and to a method for preparation of such microspheres. The invention provides stable microspheres which are preparable from inexpensive hydrolyzed vegetable protein, e.g. soybean protein, and a simple and economical method for making such microsphere. Microspheres made according to the invention display improved stability and performance in delivering biologically active materials to mammals.

According to the invention, modified hydrolyzed vegetable microspheres are prepared by dissolving hydrolyzed vegetable protein in an aqueous alkaline solution and adding a chemical modifier which reacts with free amine residues present in the hydrolyzed protein. The pH of the reaction mixture is then lowered until the modified vegetable protein precipitates out from the mixture. The recovered protein readily forms microspheres and can be used to encapsulate various cargoes such as pharmaceutical agents. The microspheres are non-toxic and can be orally or parenterally administered to mammals. Also contemplated by the present invention are dosage unit forms that include these compositions.

DETAILED DESCRIPTION OF THE INVENTION

Figure 1:
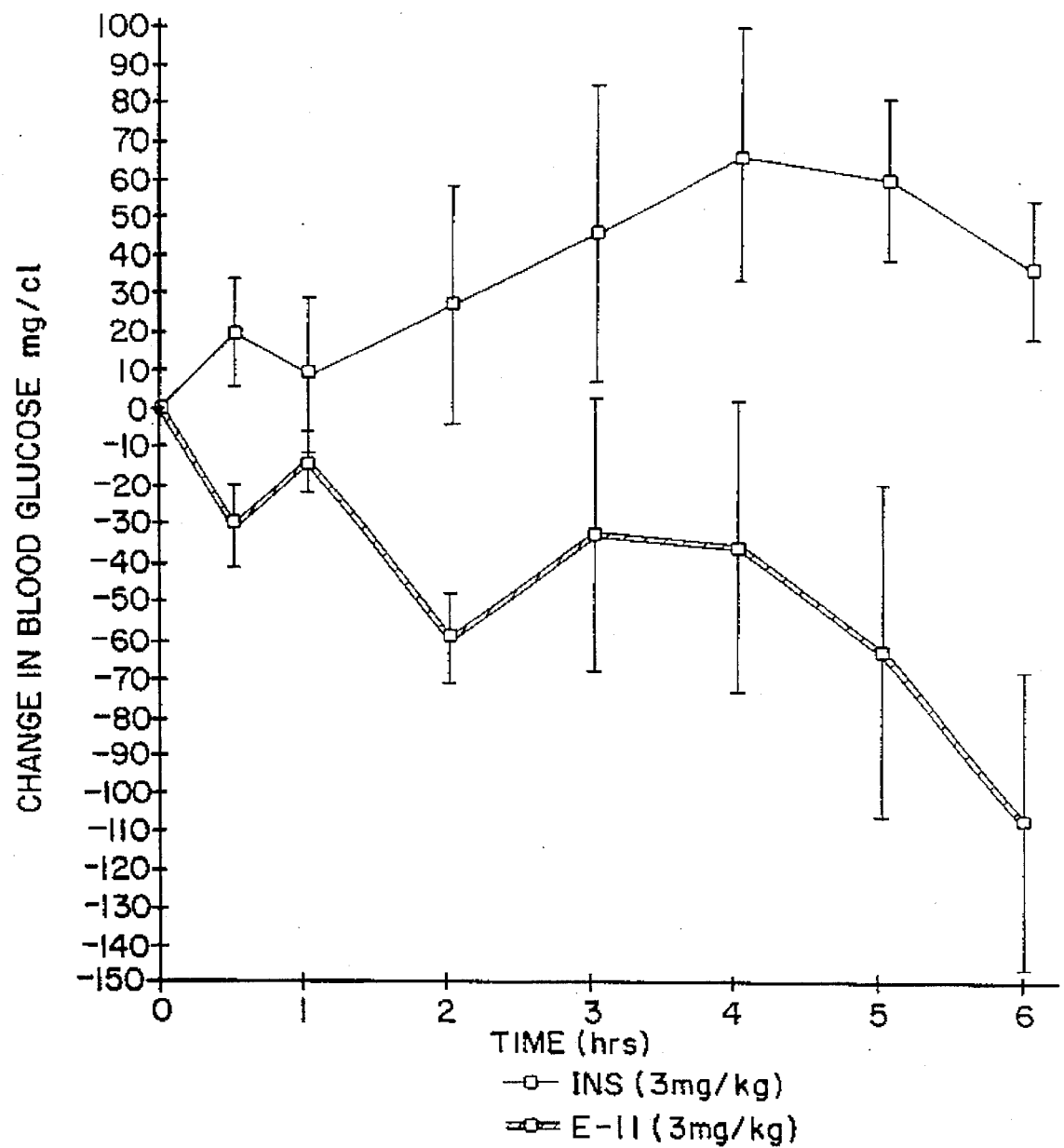
FIG. 1 illustrates levels of glucose detected in rat serum taken from rats orally administered microspheres encapsulated insulin or raw (unencapsulated) insulin as described in Example 4.

All patents, patent applications, and literatures cited in the specification are hereby incorporated by reference in their entirety. In the case of inconsistencies, the present disclosure, including definitions, will prevail.

The modified vegetable protein microspheres of the present invention may be prepared by reacting a hydrolyzed vegetable protein with a chemical modifying agent which reacts with free amino residues present in the protein. The modified vegetable protein is then converted into microspheres which encapsulate active ingredients, e.g. drugs. A number of advantages are obtainable by the present invention which include (a) the use of readily available and inexpensive starting materials and (b) a cost-effective method for preparing and isolating microsphere-producing modified proteins. The overall modification process is simple to perform and is amenable to industrial scale-up production.

The compositions of the subject invention are useful for administering biologically-active agents to any animals such as birds; mammals, such as primates and particularly humans; and insects.

According to the method of the present invention, an acid or enzyme hydrolyzed vegetable protein is useful in practicing the invention. The vegetable protein generally contains titratable carboxylic acid groups (COOH) ranging between about 3 and about 8 milliequivalents/g, preferably between about 4 and about 6 milliequivalents/g, total free amino groups ($NH_2$) ranging between about 3 and about 9 milliequivalents/g, preferably ranging between about 4 and about 7 milliequivalents/g $NH_2$. The molecular weight of the vegetable protein ranges between about 100 D and about 2000 D, preferably between about 200 and about 500 D.

Hydrolyzed vegetable protein is available from a variety of commercial sources. Non-limiting examples of such sources include Ajinomoto U.S.A., Inc. (Teaneck, N.J. 07666, U.S.A.); Central Soya Co., Inc. (Fort Wayne, Ind., U.S.A.); and Champlain Industries, Inc. (Clifton, N.J., U.S.A.) and additional companies listed in "Food Engineering Master", an annual publication of Chilton Co., Radnor, Pa. 19089, U.S.A. A particularly preferred hydrolyzed vegetable protein in practicing this invention is available from Ajinomoto U.S.A. under the tradename AJI-EKI. This product is an acid hydrolyzed liquid soybean protein which is derived from defatted soybean meal.

If desired, a dried protein extract of the hydrolyzed vegetable protein solution may be used to prepare the modified vegetable protein of the invention. The dried protein extract is preparable by extracting the hydrolyzed vegetable solution with a suitable solvent, e.g., methanol, followed by evaporating the solvent extract.

The vegetable protein is then dissolved in aqueous alkaline solution of a metal hydroxide, e.g., sodium or potassium hydroxide, and heated at a temperature ranging between about 50° C. and about 70° C., preferably between about 50° C. and about 60° C., for a period ranging between about 10 minutes and about 40 minutes, preferably about 15 minutes. The amount of alkali employed per mmole of titratable $NH_2$ in the vegetable protein generally ranges between about 2 and about 3 mmole, preferably between about 2.2 and about 2.5 mmole. The pH of the solution generally ranges between about 8 and about 13, preferably ranging between about 9 and about 10.

Thereafter, an amine modifying agent is then added to the reaction mixture while stirring. The amine modifying agents are compositions that can react with the free amino ($NH_2$) residues present in the protein. Some non-limiting examples of amine modifying agents useful in practicing the present invention include sulfonating agents such as benzene sulfonyl chloride and acylating agents such as benzoyl chloride.

The amount of amine modifying agent in relation to the quantity of hydrolyzed vegetable protein employed is based on the equivalents of total free $NH_2$ in the vegetable protein. Thus, between about 0.3 and about 1.2 equivalents of modifying agent are used for each molar equivalent of total $NH_2$ groups in vegetable protein, and preferably between about 0.6 and about 1.0 equivalents of the modifying agent for each molar equivalent of total $NH_2$ groups in the hydrolyzed vegetable protein.

In practicing the invention, the mixture of vegetable protein and modifying agent is maintained at a temperature generally ranging between about 50° C. and about 70° C., preferably between about 60° C. and about 65° C. for a period ranging between about 2 and about 5 hours.

The reaction is quenched by adjusting the pH of the mixture with a suitable acid, e.g., concentrated hydrochloric acid, until the pH reaches between about 2 and about 3. The mixture separates on standing at room temperature to form an opaque upper layer and a dark viscous lower layer. The upper layer is discarded and modified vegetable protein is collected from the lower layer by filtration. The crude modified vegetable protein is then dissolved in water at a pH ranging between about 9 and about 13, preferably between about 11 and about 13. Insoluble materials are removed by filtration and the filtrate is dried in vacuo. The yield of modified protein generally ranges between about 30 and about 60%, usually about 45%.

The modified vegetable protein of the present invention is soluble in alkaline aqueous solution (pH≧9.0); partially soluble in ethanol, n-butanol and 1:1 (v/v) toluene/ethanol solution and insoluble in neutral water. The titratable functional groups remaining in the vegetable protein after modification are as follows: carboxylic acid groups (COOH) ranging between about 1.5 and about 3.5 milliequivalents/g, preferably about 2.3 milliequivalents/g, amino groups ($NH_2$) ranging between about 0.3 and about 0.9 milliequivalents/g, preferably about 0.5 milliequivalents/g. The molecular weight of the modified vegetable protein ranges between about 200 D and about 2000 D, preferably between about 200 D and about 500 D.

The modified vegetable protein of the present invention can be used immediately to microencapsulate an active pharmacological agent or the protein can be concentrated or dried by conventional means and stored for future use.

The modified vegetable protein may be purified by fractionation on solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, a subsequent 0–500 mM sodium chloride gradient is employed. The modified vegetable protein may also be purified by extraction with a lower alcohol such as methanol, butanol, or isopropanol to remove low molecular weight contaminants.

The following procedure may be employed to make microspheres from purified modified vegetable protein. Modified vegetable protein is dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as gravity filtration over filter paper.

Thereafter, the protein solution, maintained at a temperature of about 40° C., is mixed 1:1 (V/V) with an aqueous acid solution (also at about 40° C.) having an acid concentration ranging between about 0.05N and about 2N, preferably about 1.7N. The resulting mixture is further incubated at 40° C. for a period of time effective for microsphere formation as observed by light microscopy. In practicing this invention, the preferred order of addition is to add the protein solution to the aqueous acid solution.

Suitable acids include any acid which does not (a) adversely effect the protein, e.g., chemical decomposition; (b) interfere with microsphere formation; (c) interfere with microsphere encapsulation of cargo; and (d) adversely interact with the cargo. Preferred acids for use in this invention include acetic acid, citric acid, hydrochloric acid, phosphoric acid, malic acid and maleic acid.

In practicing the invention, a microsphere stabilizing additive preferably incorporated into the aqueous acid solution or into the protein solution, prior to the microsphere formation process. The presence of such additives promotes the stability and dispersibility of the microspheres in solution.

The additives may be employed at a concentration ranging between about 0.1 and 5% (W/V), preferably about 0.5% (W/V). Suitable, but non-limiting, examples of microsphere stabilizing additives include gum acacia, gelatin, polyethylene glycol, and polylysine.

Under the above conditions, the carrier forms hollow or solid matrix type microspheres wherein the cargo is distributed in a carrier matrix or capsule type microspheres encapsulating liquid or solid cargo. If the carrier microspheres are formed in the presence of a soluble material, e.g., a pharmaceutical agent in the aforementioned aqueous acid solution, this material will be incorporated in the microspheres. In this way, one can incorporate pharmacologically active materials such as peptides, proteins, and polysaccharides as well as charged organic molecules, e.g., antimicrobial agents, which normally have poor bioavailability by the oral route. The amount of pharmaceutical agent which may be incorporated in the microsphere is dependent on a number of factors which include the concentration of agent in the microsphere forming solution, as well as the affinity of the cargo for the carrier.

Under these conditions, the modified vegetable protein molecules form hollow microspheres of less than 10 microns in diameter. If the protein microspheres are formed in the presence of a soluble material, e.g., a pharmaceutical agent in the aforementioned aqueous acid solution, this material will be encapsulated in the hollows of the microspheres and confined within the protein wall defined by the spherical structure. In this way, one can encapsulate pharmacologically active materials such as peptides, proteins, and polysaccharides as well as charged organic molecules, e.g., quinolones or antimicrobial agents, having poor bioavailability by the oral route. The amount of pharmaceutical agent which may be encapsulated by the microsphere is dependent on a number of factors which include the concentration of agent in the encapsulating solution, as well as the affinity of the cargo for the carrier.

Biologically-active agents suitable for use with carriers disclosed herein include, but are not limited to, peptides, and particularly small peptide hormones, which by themselves do not pass or only pass slowly through the gastro-intestinal mucosa and/or are susceptible to chemical cleavage by acids and enzymes in the gastro-intestinal tract; polysaccharides and particularly mixtures of mucopolysaccharides; carbohydrates; lipids; or any combination thereof. Examples include, but are not limited to, human growth hormone; bovine growth hormone; growth hormone releasing hormone; interferons; interleukin-I; insulin; heparin, and particularly low molecular weight heparin; calcitonin; erythropoietin; atrial naturetic factor; antigens; monoclonal antibodies; somatostatin; adrenocorticotropin; gonadotropin releasing hormone; oxytocin; vasopressin; cromolyn sodium (sodium or disodium cromoglycate); vancomycin; desferrioxamine (DFO); or any combination thereof.

Additionally the carriers of the present invention can be used to deliver other active agents such as pesticides and the like.

The amount of active agent in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically-active agent compositions or may contain a divided pharmacologically or biologically effective amount. The total effective amounts will be administered by cumulative units containing in total pharmacologically or biologically active amounts of biologically-active agent.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

The modified vegetable protein microspheres of the invention are pharmacologically harmless and do not alter the physiological and biological properties of the active agent. Furthermore, the encapsulation process does not alter the pharmacological properties of the active agent. While any pharmacological agent can be encapsulated within the protein microspheres, it is particularly valuable for delivering chemical or biological agents which otherwise would be destroyed or rendered less effective by conditions encountered within the body of the mammal to which it is administered, before the microsphere reaches its target zone (i.e., the area in which the contents of the microsphere are to be released) and which are poorly absorbed in the gastrointestinal tract.

The protein microspheres of the invention are particularly useful for the oral administration of certain pharmacological agents, e.g., small peptide hormones, which, by themselves, pass slowly or not at all through the gastro-intestinal mucosa and/or are susceptible to chemical cleavage by acids and enzymes in the gastrointestinal tract. Non-limiting examples of such agents include human or bovine growth hormone, interferon and interleukin-II, calcitonin, atrial naturetic factor, antigens and monoclonal antibodies.

The particle size of the microsphere plays an important role in determining release of the active agent in the targeted area of the gastrointestinal tract. Microspheres having diameters between about ≦0.1 microns and about 10 microns, preferably between about 5.0 microns and about 0.1 microns, and encapsulating active agents are sufficiently small to effectively release the active agent at the targeted area within the gastrointestinal tract. Small microspheres can also be administered parenterally by being suspended in an appropriate carrier fluid (e.g., isotonic saline) and injected into the circulatory system or subcutaneously. The mode of administration selected will, of course, vary, depending upon the requirement of the active agent being administered. Large protein microspheres (>10 microns) tend to be less effective as oral delivery systems.

The size of the microspheres formed by contacting modified vegetable protein with water or an aqueous solution containing active agents can be controlled by manipulating a variety of physical or chemical parameters, such as the pH, osmolarity or ionic strength of the encapsulating solution, and by the choice of acid used in the encapsulating process.

The vegetable protein-derived microspheres of the present invention are suitable for oral administration of peptide hormones, e.g., insulin, and polysaccharides, e.g., heparin, which otherwise would be quickly destroyed in the stomach. They also are suitable for protecting the stomach from gastric irritants, such as aspirin and NSAID'S. When such aspirin containing microspheres are orally administered, they pass through the gastrointestinal mucosa and release the aspirin far more rapidly than conventional enterically coated aspirin, which first must traverse the stomach and then must enter the bloodstream from the intestine after the enteric coating has dissolved.

The microspheres of the invention may be orally administered alone as solids in the form of tablets, pellets, capsules, and granulates suitable for suspension in liquids such as water or edible oils. Similarly, the microspheres can be formulated into a composition containing one or more physiologically compatible carriers or excipients, and which can be administered via the oral route. These compositions may contain conventional ingredients such as gelatin, polyvinylpyrrolidone and fillers such as starch and methyl cellulose. Alternatively, small microspheres (size less than 10 μm) can be administered via the parenteral route.

The following examples are illustrative of the invention but are not intended to limit the scope of the invention.

EXAMPLE 1

Modification of Soybean protein with benzene sulfonyl chloride a. Extraction of soybean protein 3.2 L of acid hydrolyzed liquid soybean protein solution (AJI-EKI, Ajinomoto U.S.A., Inc.) was reduced in vacuo to give 1440 g of solid powder. This solid was extracted 3 times with methanol (2 L per extraction). Methanol was removed from the pooled extracts by evaporation. The yield of soybean protein as a dark brown powder was 608 g. The functional groups of the soybean protein powder was titrated using conventional procedures. See, for example, "A Laboratory Manual of Analytical Methods of Protein Chemistry," Vol. 1–3, Editors P. Alexander and R. J. Block, Pergamon Press, 1960 and 1961. The soybean protein contained the following functional groups: 3.7 milliequivalents/g of COOH; 0.44 milliequivalents/g free N-terminal $NH_2$; and 3.48 milliequivalents/g total free $NH_2$. The molecular weight of the soybean protein ranged from 100 to 2000 D.

b. Modification of soybean protein

The dried soybean protein of step (a) (600 g, 2.5 equivalents of total free $NH_2$) was dissolved in 3 L of aqueous 2N potassium hydroxide solution (2.25 mole excess) and the solution was heated at 60°°C. for 30 minutes. Thereafter, benzenesulfonyl chloride (460 g, 2.60 moles) was added dropwise to the mixture and the reaction temperature was monitored so that it did not exceed 65° C. The reaction continued, with stirring, for 4 hours at 63° C. The reaction mixture cooled to room temperature, then acidified to pH 3.0 with 20% aqueous HCl solution and modified soybean protein precipitated out. The modified soybean protein was then washed twice with distilled water (1 L) and dissolved in 2N aqueous sodium hydroxide solution until a pH of 8.5–9 resulted. The solution was filtered to remove particulates and the filtrate was reduced and dried in vacuo to give dry modified product (257 g, yield=24%). The product had the following titratable groups: 2.3 milliequivalents/g of COOH; 0.2 milliequivalents/g N-terminal free $NH_2$; and 0.3 milliequivalents/g total free $NH_2$.

EXAMPLE 2

Modification of soybean protein with benzoyl chloride

A commercial hydrolyzed water solution of soybean protein (AJI-EKI, Ajinomoto U.S.A., Inc.) was used in this Example without further extraction. The protein in solution contained the following functional groups: 2.6 milliequivalents/ml of COOH and 2.0 milliequivalents/ml $NH_2$. The molecular weight of the soybean protein was approximately 6.5 kD.

To the soybean solution (240 mL, 0.5 equivalents free $NH_2$) was added 107 mL of 10N aqueous potassium hydroxide solution followed by 200 mL of distilled water. The solution was then placed in an ice bath (5° C.) and benzoyl chloride (70 g, 0.5 moles) was added dropwise within a temperature range between 10° to 25° C. The reaction mixture was then stirred for 4.5 hours at room temperature. The pH of the reaction mixture was then reduced from 13.2 to 2.8 with concentrated HCl. After being allowed to settle for 1 hour, the precipitated modified soybean protein was collected by filtration and washed with distilled water. The soybean protein was then dissolved in 2N aqueous sodium hydroxide solution to give a solution (pH 12.6) which was then evaporated to afford 48 g of dried product (% yield= 41%).

EXAMPLE 3

Preparation of Empty Microspheres With Modified Soybean Protein

This Example illustrates a method for the preparation and cleaning of empty modified soybean protein microspheres.

PROCEDURE

1. Reagents:
   a. Modified protein powder prepared as described in Example 1
   b. Anhydrous citric acid (USP)
   c. Gum acacia NF
   d. Deionized water
   e. Glacial acetic acid
2. Equipment
   a. pH meter
   b. Eppendorf pipette (0–100 ul) and tips
   c. Water bath, 40° C.
   d. liquid nitrogen
   e. lyophilization flasks
3. Preparation of Solutions:
   a. Protein solution—Dissolve 100 mg modified soybean protein in 1 ml deionized water (or multiples thereof). Filter through a Whatman #1 filter paper (if necessary) and keep at 40° C. in a water bath. This is solution A.
   b. 1.7N citric acid with 0.5% acacia—Dissolve 5 g of acacia and 109 g of citric acid in 1 liter deionized water. Incubate at 40° C. This is solution B.

4. Preparation of Microspheres:
   a. Add all of solution A to solution B rapidly in one step while swirling solution B by hand, in a 40° C. water bath.

EXAMPLE 4

Preparation of Soybean protein Microsphere containing Encapsulated Insulin

This Example describes a method for the preparation and cleaning of insulin microspheres.

PROCEDURE

1. Reagents:
   a. Modified protein powder prepared as described in Example 1
   b. Heparin
   c. Anhydrous citric acid (USP)
   d. Gum acacia NF
   e. Deionized water
   f. Desiccant
   g. Liquid nitrogen
2. Equipment:
   a. Magnetic stirrer
   b. Buret
   c. Microscope
   d. Clinical centrifuge
   Dialysis membrane tubing (Spectrum 6, 10 mm, 50,000 M.W. Cutoff)
   f. pH meter
   g. Lyophilizer (Labconco #75035)
   h. Lyophilizing flasks (150–300 mL)
   i. Rotating shell freezer
   j. Isopropanol/dry ice bath or liquid $N_2$
   k. Mortar and pestle
   l. Storage containers (500 mL)
   m. Eppendorf piper (0–100 uL)
   n. Plastic closures for dialysis tubing (Spectrum)
   o. 2 mL syringe with 0.45 μm Acrodisk
3. Preparation of Solutions:
   a. Protein Solution A* (80 mg/ml): Add 160 mg of modified soybean protein and dissolve to 1 ml with deionized water. Using a 2 ml syringe filter through a 0.45 μm Acrodisk into a 10 ml test tube. Keep at 40° C.
   * or multiples thereof.
   b. Solution B (1.7N citric acid with 1% gum): Dissolve 10 g of acacia and 109 g of citric acid in 1 liter deionized water.
   c. Solution C (Heparin solution): Dissolve heparin in Solution B at 150 mg/mL and keep at 40° C.
4. Preparation of Microspheres:
   a. Add all of solution A to solution C quickly while swirling solution C slowly, by hand, in a 40° C. water bath.
5. Cleaning of Microspheres:
   a. Transfer the suspension with a syringe (no needle) to dialysis tubing and seal with plastic closures. Tubing should be no more than 70% full.
   b. Discard any amorphous material sedimented and/or aggregated on the surface.
   c. Dialyze the microsphere suspension against acetic acid (using 20 mL of acetic acid solution per ml of microsphere suspension) while stirring the acetic acid solution with a magnetic stirrer.
   d. Replace the acetic acid solution every hour. Continue dialyzing for a total of 3 hours.
6. Lyophilization:
   a. Add one part of 50% Trehalose (Sigma) into nine parts of dialyzed microsphere solution. Flash freeze microspheres in a freeze-drying flask using the shell freezer adjusted to rotate at ca. 190 rpm and immersed in a liquid nitrogen bath.
   b. Freeze dry for 24 hours or until dry as evidenced by lack of self-cooling.
   c. Record weight of dry microspheres.
   d. Grind to a fine powder with mortar and pestle.
   e. Transfer to amber container, seal with desiccant, and store at room temperature.
7. Resuspension:
   a. Weigh the lyophilized powder and calculate the amount of protein in the powder.
   b. Add 0.85N citric acid into the lyophilized powder at 40° C. The final concentration of protein is 80 mg/ml.

EXAMPLE 5

Evaluation of Insulin Microspheres in Rats

In this Example, the insulin microspheres prepared in accordance with Example 3 were evaluated in rats. Twelve rats were divided into two groups as follows:

1. oral insulin microspheres: 3 mg insulin/kg body weight by oral gavage (six rats);
2. Raw insulin (no encapsulation): 3 mg insulin/kg body weight by oral garage (six rats).

Oral gavage dosing of rats was performed. Insulin microspheres were prepared immediately prior to dosing and Group 1 rats each receive an appropriate dosage of the microsphere suspension. Group 2 rats received the unencapsulated insulin. Approximately 0.5 ml of blood was withdrawn from each rat just prior to dosing ("0" time) and 1 to 6 h post-dosing. Serum from the blood samples were stored at −20° C.

The glucose levels of thawed serum taken from the rats were analyzed by conventional methods. As shown in FIG. 1, sharp decreases in serum glucose levels were observed in groups 1 rats receiving the encapsulated insulin. In contrast, the serum glucose levels in group 2 rats slightly increased from t=0. The results show that encapsulated insulin had a greater biological effect, when administered orally, in contrast to unencapsulated insulin.

EXAMPLE 6

Preparation of Microsphere Encapsulated Calcitonin

Encapsulation of salmon calcitonin in soybean protein microspheres were performed in the same manner described in Example 3. Calcitonin was obtained from Sandoz (Basil, Switzerland) and a 150 mg/mL calcitonin solution in 1.7N citric acid solution with 1% gum was prepared as described in Example 3.

EXAMPLE 7

Evaluation of Calcitonin Microspheres in Rats

In this Example, the calcitonin microspheres prepared in accordance with Example 5 were evaluated in rats. Twelve rats were divided into two groups as follows:

1. oral calcitonin microspheres: 60 μg calcitonin/kg body weight by oral gavage (six rats).
2. oral unencapsulated microspheres: 60 μg calcitonin/kg body weight by oral gavage (3 rats) (Control).

Oral gavage dosing of rats was performed. Calcitonin microspheres were prepared immediately prior to dosing and Group 1 rats received an appropriate dosage of the microsphere suspension. Group 2 rats received the unencapsulated calcitonin. Approximately 0.5 ml of blood was withdrawn from each rat just prior to dosing ("0" time) and 1 h, 2 h and 3 h post-dosing. Serum from the blood samples were stored at −20° C.

Figure 2:
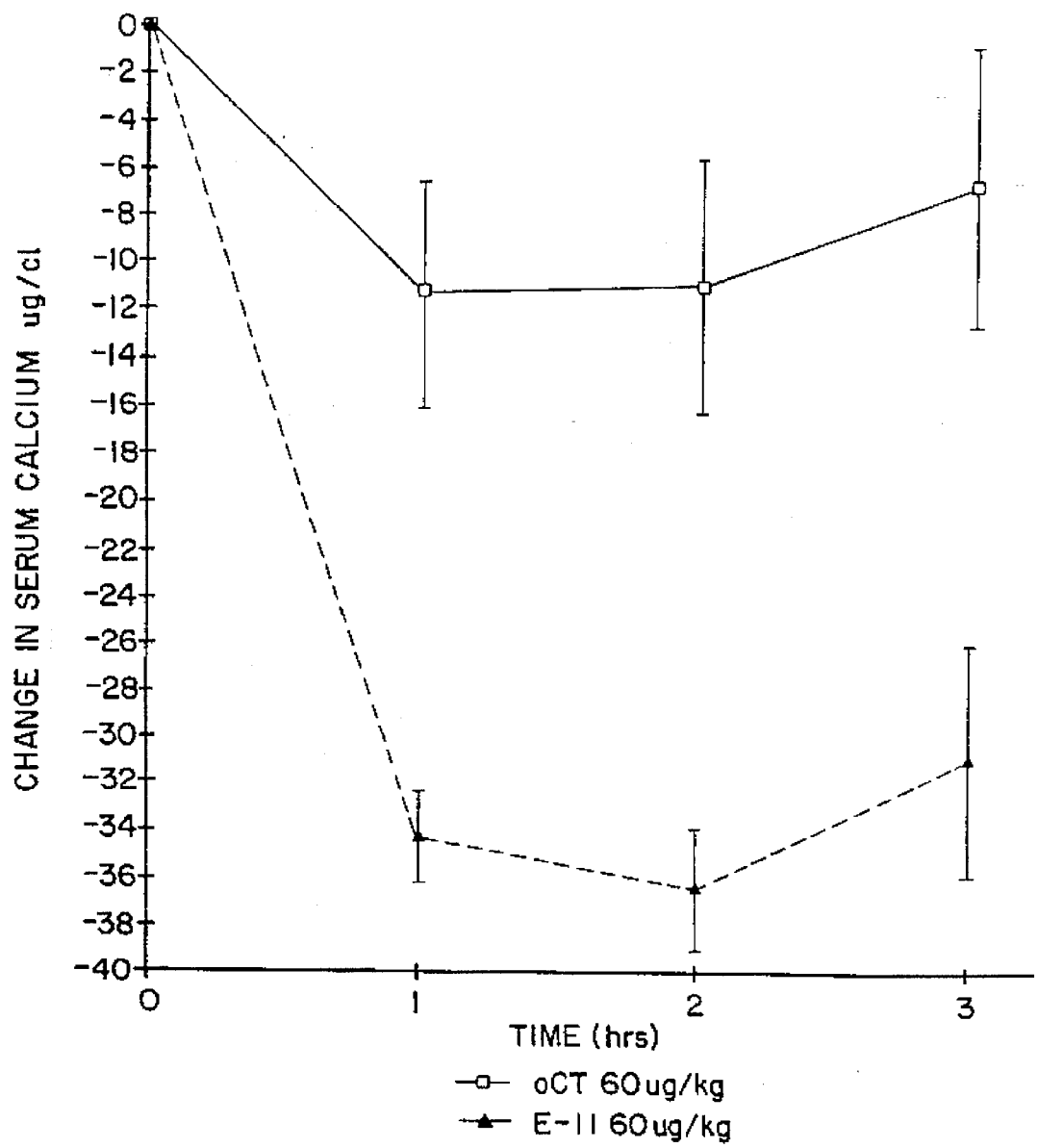
FIGS. 2 and 5 illustrate rat serum calcium levels after oral administration of calcitonin and calcitonin encapsulated in the vegetable protein microspheres of the present invention as described in Examples 5 and 8.
Figure 3:
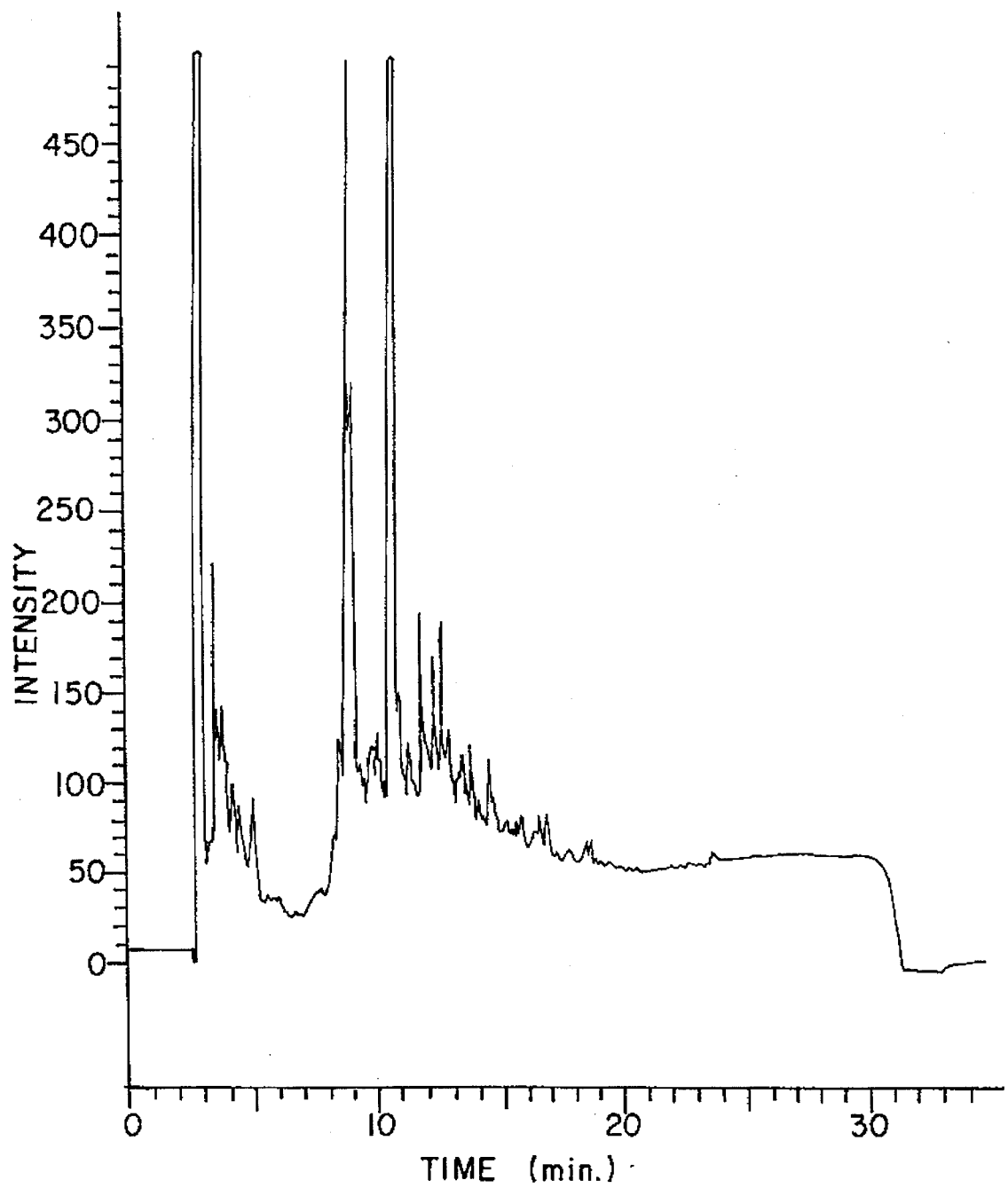
FIG. 3 illustrates an HPLC trace of the hydrolyzed vegetable protein before modification.
Figure 4:
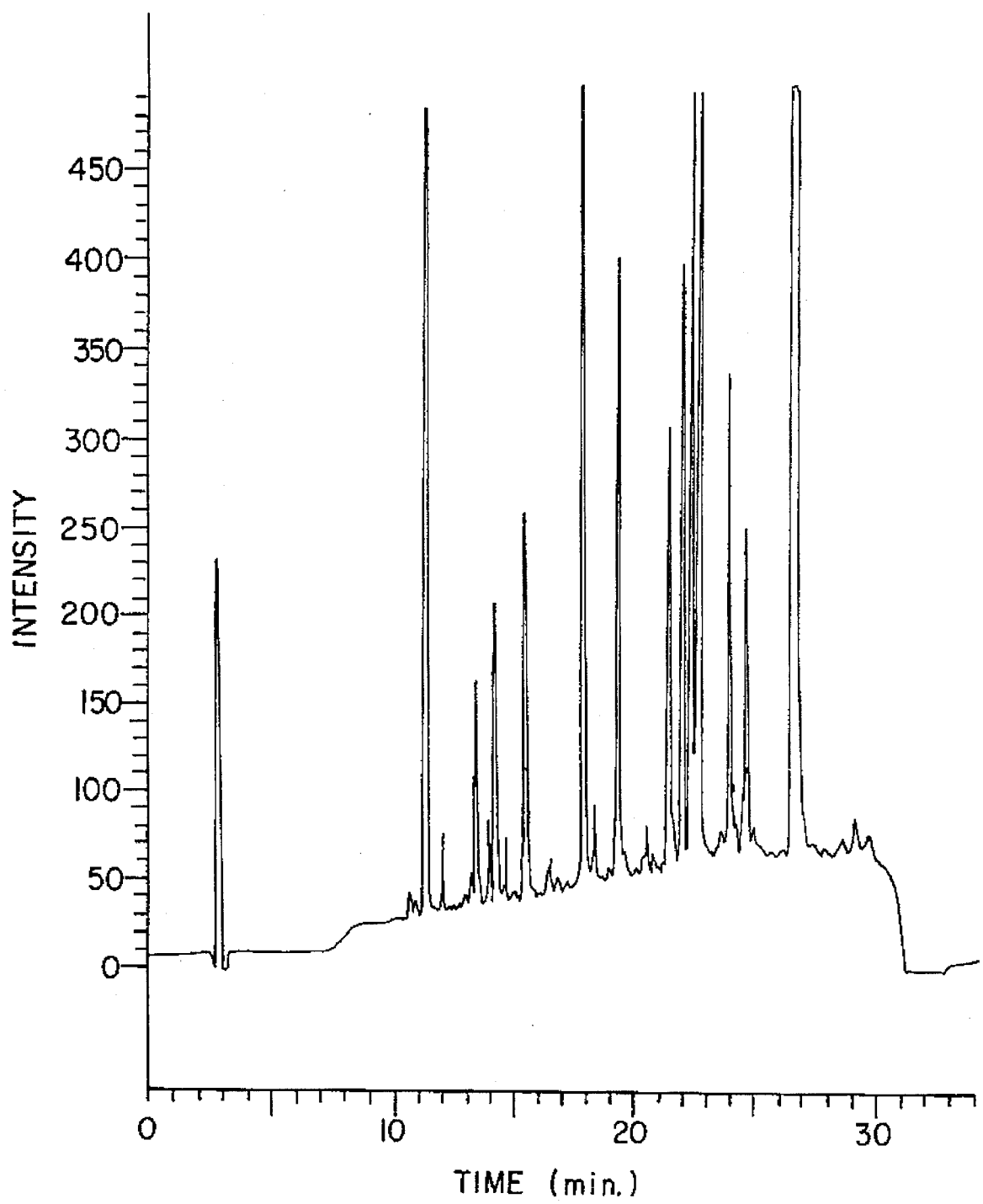
FIG. 4 illustrates the change in the hydrolyzed vegetable protein after modification with benzene sulfonyl chloride in an HPLC trace.

The calcium levels of thawed serum taken from group 1 and 2 rats were analyzed by conventional methods. As shown in FIG. 2, sharp decreases in serum calcium levels were observed in group 1 rats receiving the encapsulated calcitonin. In contrast, the calcium levels in group 2 rats slightly decreased from t=0. The results show that encapsulated calcitonin had a greater biological effect, when administered orally, in contrast to unencapsulated calcitonin.

EXAMPLE 8

Figure 5:
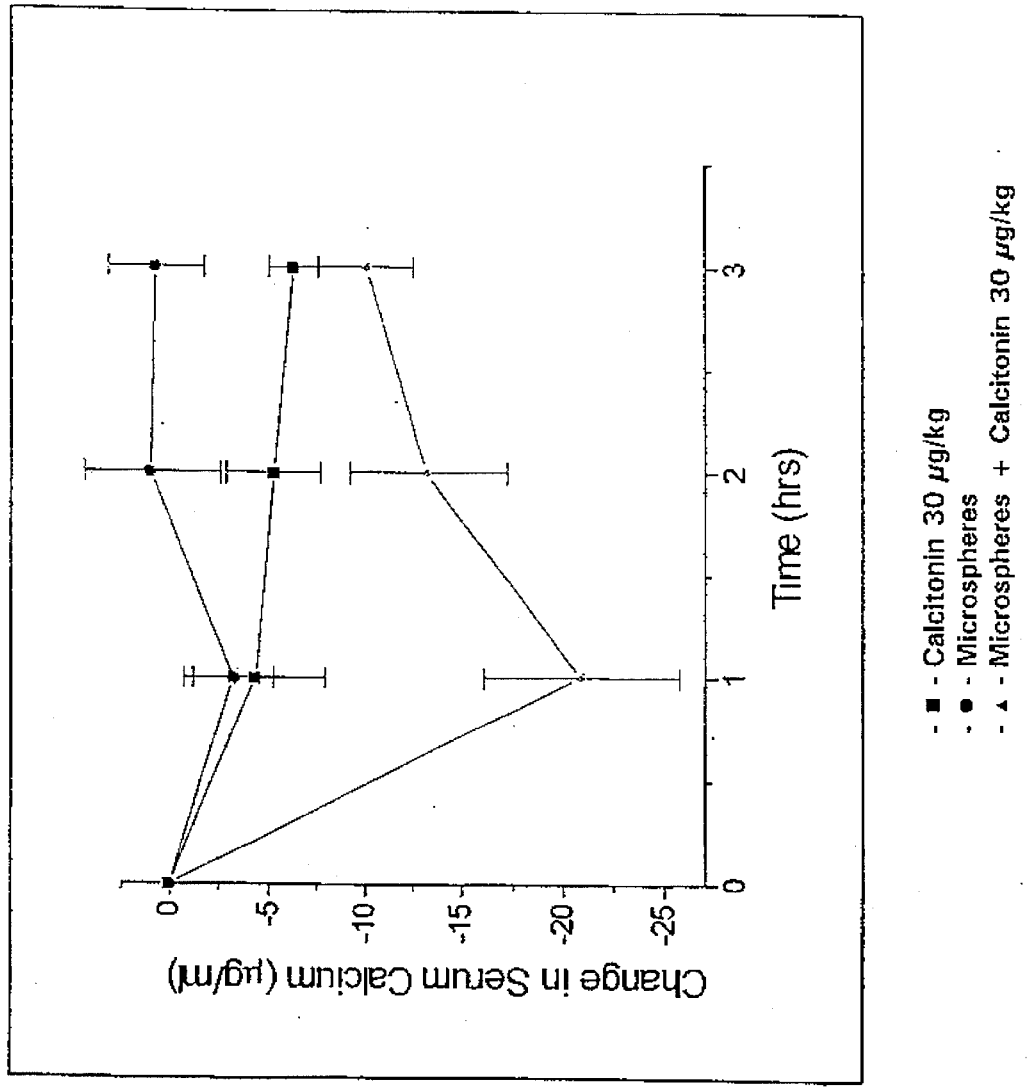

Encapsulation of salmon calcitonin in soybean protein microspheres was performed in the same manner described in Example 3. The dosage administered to the rats was 30 μg/kg. Three groups of rats were tested. The first group was tested with calcitonin alone. The second group was given microspheres alone. The third group was given the encapsulated calcitonin. The results are illustrated in FIG. 5. The results show that encapsulated calcitonin, when administered orally, had a greater biological effect in contrast to unencapsulated calcitonin.

What is claimed is:

1. A microsphere for encapsulating an active agent, said microsphere comprising an acid hydrolyzed soybean protein modified with an amine reactive modifying agent.

2. The microsphere according to claim 1, wherein said microsphere has a diameter equal to or less than 10 microns.

3. The microsphere according to claim 1, wherein said amine reactive modifying agent is selected from the group consisting of benzene sulfonyl chloride and benzoyl chloride.

4. The composition comprising a biologically-active agent encapsulated with an acid hydrolyzed soybean protein microsphere, said microsphere comprising a biocompatible protein wall comprising a hydrolyzed vegetable protein modified with an amine reactive modifying agent.

5. The composition according to claim 4, wherein said amine reactive modifying agent is selected from the group consisting of benzene sulfonyl chloride and benzoyl chloride.

6. The composition according to claim 4, wherein said biologically-active agent is selected from the group consisting of a peptide, a mucopolysaccharide, or any combination thereof.

7. The composition according to claim 4, wherein said biologically-active agent is human growth hormone.

8. A dosage unit form comprising
   (A) a composition according to claim 4; and
   (B)
      (a) an excipient,
      (b) a diluent,
      (c) a disintegrant,
      (d) a lubricant,
      (e) a plasticizer,
      (f) a colorant,
      (g) a dosing vehicle, or
      (h) any combination thereof.

9. A dosage unit form according to claim 8 comprising a tablet, a capsule, or a liquid.

10. The composition according to claim 4, wherein said peptide is human growth factor.

11. The composition according to claim 4, wherein the biologically active agent is a polysaccharide.

12. The composition according to claim 11, wherein said polysaccharide is heparin.

13. The method according to claim 4, wherein said microspheres are hollow and said biologically-active agent is encapsulated therein.

* * * * *